United States Patent [19]

Mitsui et al.

[11] Patent Number: 4,588,846
[45] Date of Patent: May 13, 1986

[54] PROCESS FOR PRODUCING CYCLIC ALCOHOL

[75] Inventors: Osamu Mitsui; Yohei Fukuoka, both of Okayama, Japan

[73] Assignee: Asahi Kasei Kogyo Kabushiki Kaisha, Osaka, Japan

[21] Appl. No.: 669,976

[22] Filed: Nov. 9, 1984

[30] Foreign Application Priority Data

Nov. 9, 1983 [JP] Japan .................. 58-209150
Nov. 9, 1983 [JP] Japan .................. 58-209148

[51] Int. Cl.$^4$ .................................................. C07C 35/08
[52] U.S. Cl. ........................... 568/835; 568/822; 568/825; 568/832; 568/895; 568/897
[58] Field of Search ............ 568/821, 822, 832, 835, 568/825, 895, 897

[56] References Cited

U.S. PATENT DOCUMENTS

| | | | |
|---|---|---|---|
| 4,214,107 | 7/1981 | Chang | 568/897 |
| 4,324,940 | 4/1982 | Dessau | 568/466 |
| 4,499,314 | 2/1985 | Okumar et al. | 568/897 |
| 4,507,512 | 3/1985 | Okumar et al. | 568/897 |

FOREIGN PATENT DOCUMENTS

| | | | |
|---|---|---|---|
| 45323 | 10/1968 | Japan | 568/897 |
| 70828 | 1/1982 | Japan | 568/897 |
| 124723 | 7/1983 | Japan | 568/897 |
| 194828 | 12/1983 | Japan | 568/821 |

*Primary Examiner*—Werren B. Lone
*Attorney, Agent, or Firm*—Sughrue, Mion, Zinn, Macpeak & Seas

[57] ABSTRACT

A process is provided for producing a cyclic alcohol by catalytic hydration of a cyclic olefin in a liquid phase, which comprises using as a catalyst a zeolite having a population ratio of acid sites on the external surface to total acid sites of 0.07/1 or more, conducting the hydration reaction in a reaction zone in the copresence of an oil phase mainly containing cyclic olefin and an aqueous phase mainly containing water and the catalyst while controlling the cyclic alcohol produced so that the concentration thereof in the oil phase is more than that in the aqueous phase, and separating and recovering the cyclic alcohol produced from the oil phase.

18 Claims, 1 Drawing Figure

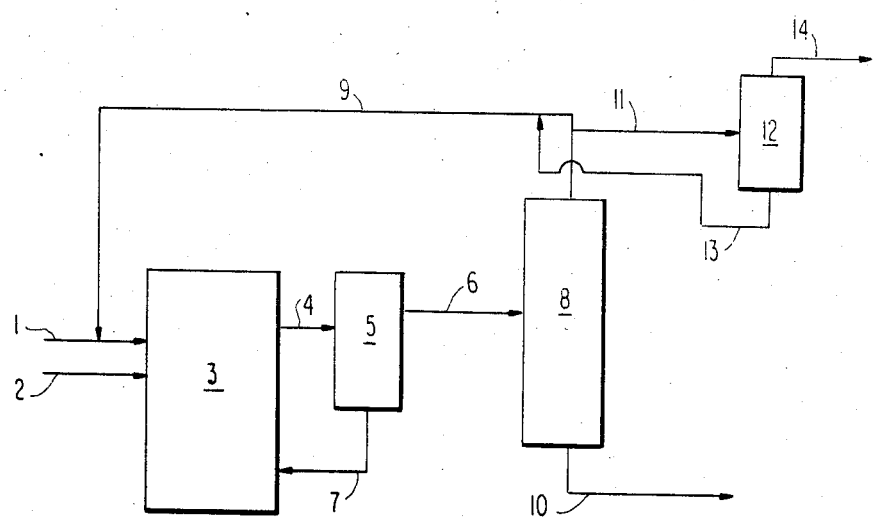

PROCESS FOR PRODUCING CYCLIC ALCOHOL

FIELD OF THE INVENTION

This invention relates to a novel process for producing a cyclic alcohol by catalytic hydration of a cyclic olefin.

BACKGROUND OF THE INVENTION

As processes for producing cyclic alcohols by hydration of cyclic olefins, processes of indirect or direct hydration reaction using mineral acids, particularly sulfuric acid, have conventionally been known. As other homogeneous catalysts for the reaction, aromatic sulfonic acids as described in Japanese Patent Publication No. 8104/68 and Japanese Patent Publication No. 16123/68, heteropolyacids such as phosphotungstic acid or phosphomolybdic acid as described in Japanese Patent Application (OPI) No. 9746/78 (the term "OPI" as used herein refers to a "published unexamined Japanese patent application"), etc., have also been proposed.

However, use of these homogeneous catalysts involves serious problems due to the corrosiveness of the catalysts with respect to materials used for reactors or the like and deterioration of the catalysts. In addition, since the reaction product produced with the aid of these catalysts exists mostly in an aqueous phase, separation and recovery of the product from the aqueous phase requires complicated procedures and much energy.

As a process for overcoming these defects, it has been proposed to use solid catalysts, for example, ion exchange resins as described in Japanese Patent Publication Nos. 15619/63 and 26656/69.

However, such ion exchange resins have the problem of deterioration of catalyst activity due to reduction in size of the resin by mechanical disintegration and due to insufficient heat resistance of the resin, thus being unable to provide stable catalyst activity over a long period of time.

Further as a process of using a solid catalyst, it has been proposed to use crystalline aluminosilicates. Crystalline aluminosilicates are insoluble in water and have excellent mechanical strength and heat resistance, thus being expected to be utilized as industrial catalysts. Thus, Japanese Patent Publication No. 45323/72 proposes a process for producing alcohols by hydration of olefins using dealkalized mordenite, clinoptilolite, or faujasite type zeolite as a catalyst.

Japanese Patent Publication No. 45323/72 describes in Example 4 an example of using cyclohexene as the cyclic olefin. According to the description of Example 4, the reaction is conducted in an autoclave at a reaction temperature of from 200° to 210° C. for a reaction time of from 10 to 15 hours to obtain a conversion of water to cyclohexanol of as low as 0.05 to 0.06%. Calculation of the conversion of cyclohexene to cyclohexanol based on the above description gives a conversion of 0.07 to 0.08% and, in turn, calculation in the same manner of the concentration of cyclohexanol in water based on this conversion gives a concentration of about 0.3%. No description appears therein as to selectivity of reacted cyclohexene to cyclohexanol and production of by-products. With the hydration reaction of propylene or 1-butene also described in the same Example, conversions of the straight chain olefins to corresponding alcohols are as high as 10 to 20% and 4 to 7%, respectively (calculated based on the conversions of water as in the above-described case, with the concentrations of the resulting alcohols in water, calculated based on these conversions, being 9 to 20% and 4 to 6%, respectively). In contrast, the Example shows that hydration reaction of cyclohexene to cyclohexanol is not practical due to too low conversion to cyclohexanol.

U.S. Pat. No. 4,214,107 describes examples of gaseous phase catalytic hydration reaction of straight chain olefins such as ethylene, propylene, etc., using HZSM-5 (proton-exchanged ZSM-5 made by Mobil Oil Corporation). However, no descriptions are found therein with respect to cycloolefins.

U.S. Pat. No. 4,324,940 proposes a process of selectively reacting smaller olefins by effecting acid-catalyzed reactions of a mixed stream composed of smaller olefins and larger olefins using a crystalline zeolite. According to the description in this patent, the acid-catalyzed reactions include hydration reactions, and the olefins include cycloolefins. However, no examples thereof are given therein. In addition, it is described therein, from col. 6, line 4 up to col. 7, line 3, that zeolites of larger crystal size are more effective.

Japanese Patent Application (OPI) No. 70828/82 proposes a process for producing alcohols by hydration of olefins using specific crystalline aluminosilicates of Mobil Oil Corporation, such as ZSM-5 or ZSM-21. However, no examples of reacting cyclic olefins as olefins are given therein. Example 1 shows a reaction of propylene as a straight chain olefin, wherein the reaction is conducted at 200° C. for 2 hours followed by an after-treatment of removing unreacted propylene and the catalyst to obtain an aqueous filtrate containing 8.7 wt% isopropanol. On the other hand, Example 3 shows a reaction of 1-butene, wherein the reaction is conducted at 160° C. for 2 hours followed by the same after-treatment as described above to obtain an aqueous filtrate containing as low as 1.2 wt% sec-butyl alcohol.

Japanese Patent Application (OPI) No. 124723/83 proposes a process for producing alcohols by hydration of olefins using as a catalyst a partly dealuminated zeolite whose exchangeable ions have been wholly or partly exchanged with protons, an ion of an element of the group II or VIII of the Periodic Table, or of an earth metal element or rare earth element. However, reaction examples on cyclic olefins are not described therein. As examples of straight chain olefins, Example 1 shows a reaction of n-butylene, wherein the reaction is conducted at 170° C. for 2 hours followed by removing unreacted n-butylene and the catalyst to obtain a filtrate containing at most 3.4 wt% sec-butyl alcohol.

In view of the difference in reactivity between straight chain olefins and cycloolefins shown in Japanese Patent Application (OPI) No. 4532/72 and the difference in reactivity between straight chain olefins shown in the Examples therein, extremely low reactivity is expected in the synthesis of cyclic alcohols from cyclic olefins using the catalysts specified by the aforesaid U.S. Pat. Nos. 4,214,107 and 4,324,940 and Japanese Patent Application (OPI) Nos. 70828/82 and 124723/83. In addition, there are no information therein on side reactions or other problems that occur.

Where the conversion of cyclic olefin to cyclic alcohol is low, there also arises a problem with respect to recovery of the cyclic alcohol produced. That is, in contrast to alcohols derived from straight chain olefins, all cyclic alcohols have higher boiling points than the other reactant, water, and hence water must be first removed from the system, followed by distillation or the like to separate and recover the cyclic alcohol. Thus, the recovery requires much heat, which leads to seriously increased costs and brings about a problem with respect to practical utility. Further, with cyclic alcohols forming azeotropic compositions with water, the boiling points of the azeotropic compositions are close to that of water, which similarly requires, in view of the large proportion of water in the compositions, seriously increased costs for separation and recovery of cyclic alcohols.

SUMMARY OF THE INVENTION

As a result of intensive investigations to solve the above-mentioned problems, it has now been found that cyclic alcohols can be easily obtained by effecting catalytic hydration of cyclic olefins in a specific manner according to the present invention using the catalyst of the present invention.

That is, the present invention is a process for producing a cyclic alcohol by catalytic hydration of a cyclic olefin in a liquid phase, which comprises using as a catalyst a zeolite having a population ratio of acid sites on external surface to total acid sites of 0.07/1 or more, conducting the hydration reaction in a reaction zone in the copresence of an oil phase mainly containing the cyclic olefin and an aqueous phase mainly containing water and the catalyst while controlling the cyclic alcohol produced so that the concentration thereof in the oil phase is more than that in the aqueous phase, and separating and recovering the produced cyclic alcohol from the oil phase.

BRIEF DESCRIPTION OF THE DRAWING

The attached drawing illustrates an example of a flow sheet for practicing the present invention, wherein numeral 1 designates a feed pipe, 2 a feed pipe, 3 a reactor, 4 a discharge pipe, 5 a separator, 6 a discharge pipe, 7 a recycle pipe, 8 a distillator, 9 a low boiling fraction-discharging pipe, 10 a high boiling fraction-discharging pipe, 11 a pipe for introduction into a purifier, 12 a purifier, 13 a purified liquid-discharging pipe, and 14 a discharge pipe.

DETAILED DESCRIPTION OF THE INVENTION

The characteristic of the present invention is that, in spite of the low activity of ordinary zeolites, the catalyst of the present invention shows a high activity in catalytic hydration of cyclic olefins and enables production of cyclic alcohols in substantially good yield. In addition, the alcohols produced can be very easily separated from water and the catalyst according to the process of the present invention, which separation has been difficult in the prior art.

The present invention will be described in more detail below.

The catalyst in accordance with the present invention has the advantages that it remarkably enhances the conversion rate of cyclic olefin to cyclic alcohol, and that it reduces side reactions. For example, in the case of using cyclohexene as cyclic olefin, side reactions caused in the prior art include isomerization to methylcyclopentenes, such as 1-methylcyclopentene, 3-methylcyclopentene, 4-methylcyclopentene, etc., and these isomerized methylcyclopentenes are in turn converted to methylcyclopentanol, etc., by the hydration reaction. In addition, production of high boiling materials by polymerization of cyclohexene to its dimer or the like, production of diene compounds by dehydrogenation, and production of further reacted high boiling materials are observed. Further, ethers or the like derived from desired cyclohexanol are also produced. Most of these side reactions are scarcely or never observed with reactions of straight chain olefins. The side reactions are caused by the unstableness of cyclic olefins. The use of the catalyst in accordance with the present invention serves to remarkably reduce these side reactions. Further, this effect leads to a remarkable preclusion of reduction of the catalyst activity with time, and, as a result, enables maintaining high activity and high selectivity over a long period of time. These are unexpected and surprising facts.

The population of the total acid sites of zeolites synthesized by various processes were measured through amounts of adsorbed amines having comparatively small molecule sizes such as ammonia, methylamine or, in some cases, pyridine. As a result, it was found that the population of acid sites varied depending upon the kind of zeolite, and, with the same kind of zeolites, upon the molar ratio of silica to alumina or the like contained therein. On the other hand, the population of acid sites on the external surface of zeolite micropores were measured in the same manner as described above, except for using amines having larger molecule sizes such as 4-methylquinoline, 2,4-dimethylquinoline, tributylamine triperfluorobutylamine, or the like as the amines and, as a result, it was found that, where particle sizes of primary particles are different, even zeolites of the same kind having the same molar ratio of silica to alumina or the like contained therein are greatly different from each other in the population of external acid sites, even though the population of the total acid sites is the same. That is, the population of the external surface acid sites varies depending upon the size of zeolite particles, and zeolites of smaller particle size possess more external surface acid sites per unit weight, and therefore tend to have a larger population ratio of external surface acid sites to total acid sites. When zeolites having different particle sizes were subjected to measurement of surface area according to the ordinary physical adsorption method, almost the same surface areas were obtained. The reasons for the effects of the present invention obtained by using zeolites with a large population ratio of external surface acid sites to total acid sites are not clear, but may be as follows. Since cyclic olefins to be fed as reactants of the present invention have comparatively large molecule sizes and the reaction is conducted at comparatively low temperatures in a liquid phase, the degree of freedom of the molecules is more restricted, and they difficultly approach acid sites inside the catalyst. As a result, the reaction tends to proceed at the acid sites on the external surface. This may also be surmised from the fact that reaction rates of the hydration reaction of cyclic olefins conducted in a known manner are much slower than that of straight chain olefins, which may be attributed to the low reactivity of cyclic olefins themselves and the small population of reaction sites on the catalyst described above.

On the other hand, when straight chain olefins are reacted under the conditions of the present invention, the effects provided by zeolites having a large population ratio of external surface acid sites to total acid sites, characteristic of the present invention, are scarcely shown. This fact suggests that molecules having comparatively small molecule sizes and moving comparatively freely in water, such as straight chain olefins, or reaction systems wherein molecules can freely move such as a gaseous phase reaction system, can utilize the total acid sites as active sites. Also, since straight chain olefins originally suffer less side reactions than cyclic olefins, the effect of the present invention on this point is not observed, either.

However, the effects of the present invention cannot yet be fully explained by the above-described reasons.

As is described in Japanese Patent Application (OPI) No. 70828/82, page 2, solid acid catalysts are known to suffer serious reduction in activity when in contact with liquid state water. One of the reasons therefor is seriously decreased contact between the catalyst and the reactant in water. Primary particles of zeolites of the present invention having a large population ratio of external surface acid sites to total acid sites are extremely small in size as a result of the large population ratio. Fine catalysts can be easily made into a homogeneous slurry, which greatly facilitates the contact between the catalyst and the reactant and migration of the reactant and the reaction product on the catalyst, seemingly serving to accelerate the reaction. In addition, the above-described situation serves to relatively depress diffusion of the reactant into the interior of the catalyst particles, leading to depressed side reactions. In zeolite particles, the external surface and the interior portion thereof are generally different from each other in the silica-to-alumina molar ratio, with the external surface containing relatively more alumina. However, fine zeolites are known to be composed of the external surface and the interior portion having almost the same silica-to-alumina molar ratio. From this, it is surmised that fine zeolites and zeolites not being fine are different particularly in fine structure of the external surface and, therefore, different in the very active sites. Thus, the effects of the present invention are partly but greatly derived from the above-described fact.

As an example of using fine zeolites, U.S. Pat. No. 3,926,782 describes their effect on modification of hydrocarbons, etc., which, however, is essentially different from the effect of the present invention obtained in the reaction of cyclic olefin in water.

Zeolites to be used in the present invention include mordenite, faujasite, clinoptilolite, zeolite L, ZSM type zeolites of Mobil Oil Corporation (U.S. Pat. Nos. 3,702,886, 3,832,449, 4,209,499 and 4,079,096, West German Pat. Nos. 2,435,860, 2,817,575 and 2,817,576, and European Pat. Nos. 15,132, 12,572 and 14,059, etc.), chabazite, erionite, etc. In addition, AZ-1 (Japanese Patent Application (OPI) No. 128210/84, TPZ-3 (Japanese Patent Application (OPI) No. 110419/83), Nu-3 (U.S. Pat. No. 4,372,930), Nu-5 (U.S. Pat. No. 4,420,467), Nu-6 (U.S. Pat. No. 4,397,825), Nu-10, (European Pat. No. 65,400), etc., are also effective. In addition to the above-described aluminosilicates, borosilicates, ferrosilicates, chromosilicates, gallosilicates, etc., are effective as well. In particular. synthesized zeolites are effective, since they can be adjusted to possess more acid sites on the external surface thereof by controlling synthesis conditions.

These usable zeolites are natural or synthetic zeolites having ion exchangeable ability and, when calcined to remove water of crystallization they form regular and definite voids. The crystals to be used in the present invention which have large ratios of acid sites on external surface to total acid sites in number and which, as a result, are fine-grained, are prepared by fine-graining the synthesized zeolites in the stage of or after synthesis of them or fine-graining the natural zeolites by mechanical or chemical treatment. It is easy to fine-grain zeolites in the stage of the synthesis thereof.

The zeolites to be used in the present invention which have large ratios of external surface acid sites to total acid sites in number, for example, crystalline aluminosilicates, are not particularly limited as to the silica-to-alumina molar ratio, but aluminosilicates having a silica to alumina molar ratio of 10/1 or more are preferable, with those having a molar ratio of 20/1 or more being particularly preferable. As the silica to alumina molar ratio increases, the acid strength of each acid site functioning as an active site for the hydration reaction is enhanced, but the population of acid sites is decreased. Therefore, usually those of up to 300/1 in the silica to alumina molar ratio are used. In the case of using cyclic olefins as reactants, the use of the zeolite as such does not necessarily enhance the activity and selectivity of the hydration reaction due to the characteristics, reactivity, etc., of the olefins. However, remarkable improvement of the activity and selectivity are obtained by increasing the population of the acid sites on the external surface of zeolites to thereby increase the number of reaction active sites, thus such catalysts being quite advantageous. Such effects are also obtained with other zeolites such as borosilicates, ferrosilicates, chromosilicates, gallosilicates, etc.

The zeolites to be used in the present invention have a population ratio of acid sites on the external surface to total acid sites of 0.07/1 or more, preferably 0.2/1 or more, and more preferably 0.3/1 or more. However, when the population of the external surface acid sites is increased too much, zeolites cannot hold their structures as zeolites, and the acid sites undergo changes in properties. Therefore, the proportion of the external surface acid sites in number based on the total acid sites is preferably not more than 0.7.

Primary particles (morphologically single particles) of the zeolites to be used in the present invention which have a large ratio of external surface acid sites to total acid sites in number are, as a result of the large ratio, fine particles. Usually, zeolites of less than 0.5 $\mu$m in primary particle size are used, with zeolites of up to 0.1 $\mu$m being preferable and those of up to 0.05 $\mu$m being more preferable. Zeolites of finer particle sizes exhibit greater effects according to the present invention, but, in order to maintain the crystalline structure as a zeolite and to possess active acid sites, zeolites of 0.005 $\mu$m or more in particle size are particularly effective. The particle size of the primary particles of zeolites can be measured in a conventional manner using an electron microscope. The primary particles may be in various forms. For example, there are included needle-like crystals and thin plate (e.g., disc-like) crystals. With such crystals, the particle size means the narrowest width or thickness. The particle size as used in the present invention means an arithmetic mean particle size and is measured by a scanning electron microscope (Hitachi X-650, produced by Hitachi Ltd.) in the manner that samples on aluminum carriers are coated by vaporizing with carbon and then with a layer of gold/palladium alloy and the samples are observed at the magnification of from 2,000 to 50,000.

The fine-grained particles sometimes agglomerate to form secondary particles. Such formation of secondary particles have nothing to do with the effect of the present invention, and the particles are similarly effective.

More preferable zeolites to be used in the present invention which have large ratios of external surface acid sites to total acid sites in number are those which have a high molar ratio of silica to alumina or the like, which can be easily synthesized. For example, there are illustrated ZSM type zeolites, AZ-1, borosilicates, ferrosilicates, chromosilicates, gallosilicates, etc. Mordenite, faujasite, and clinoptilolite are also effective since they do not require difficulty available organic polar compounds upon their synthesis.

It is effective to subject the fine-grained crystalline aluminosilicate to be used in the present invention to the procedure of removing part of alumina before being used. However, it is not preferable that the crystalline aluminosilicates undergo change in crystal structure by the procedure, and therefore the removing procedure is preferably conducted with stably keeping the strength. In the reaction of cyclic olefins in accordance with the present invention, external surface of the zeolites is particularly of importance, and preferential removal of alumina from the external surface is particularly preferable. As such procedure, it is particularly effective to treat with a compound such as an organic acid or a chelating compound having a size sufficient to make it difficult for molecules thereof to enter into the inside of crystalline aluminosilicate particles. Further, it is effective to introduce silica from an outside source into the positions of the skeletal structure of zeolites that have been partly freed of alumina.

In the present invention, zeolites having a large population of acid sites on external surface are directly added to a reaction system and effectively used in a slurry state. Alternatively, the fine-grained zeolites may be granulated and effectively used, for example, as pellets. In the latter case, separation of the reaction product from the catalyst is facilitated, but there arises a problem of loss of part of the effective of the present invention, such as fluidity of catalyst and contact efficiently between catalyst and reactant.

In the present invention, zeolites having a large external surface acid sites population are very fine primary particles. In the case of using such zeolites as fine particle catalysts, separation of the catalysts from the reaction product imposes a difficult problem. For example, as is described in Japanese Patent Application (OPI) Nos. 70828/82 and 124723/83, alcohols produced from straight chain olefins, such as isopropanol and isobutanol, are effectively taken out as a top distillate, though there remains a problem of handling a slurry containing the catalyst. In the case of using cyclic olefins as reactants, recovery of produced high boiling cyclic alcohols from the aqueous phase is extremely difficult, and separation of the alcohols from the fine-grained catalyst cannot be effected by ordinary procedures such as filtration.

As a result of careful observation of the process of the present invention, the inventors have found the following fact. That is, in practicing the process of the present invention in a liquid phase, two phases consisting of an oil phase and an aqueous phase are formed in the reaction system when the cyclic olefin is used in an amount employed for conducting the process of the present invention due to the extremely low solubility of the reactant cyclic olefin in water (for example, solubility of cyclohexene in water at 25° C. being 0.02 wt%). The reaction proceeds in a stirred and mixed state, and, if stirring is stopped, the reaction solution again separates into the two phases. In this situation, the fine-grained zeolite used in the present invention exists in the aqueous phase and not at all in the oil phase. It has been found that, when the cyclic olefin is subjected to the hydration reaction using the fine-grained catalyst of the present invention under the above-described conditions, the cyclic alcohol produced exists mostly in the oil phase containing unreacted cyclic olefin, as is different from the case of straight chain alcohols.

Where cyclohexanol is produced using cyclohexene as the cyclic olefin; the cyclohexanol produced exists mostly in the aqueous phase only at the very initial stage of the reaction, i.e., at the stage where the amount of cyclohexanol produced is extremely small; however, with the increase in the amount of cyclohexanol produced, concentration of cyclohexanol in the oil phase increases but that in the aqueous phase scarcely increases. As a result, most of the cyclohexanol produced exists in the oil phase after the initial stage. In the example of using cyclohexene as described in Japanese Patent Publication No. 45323/72, conversion to cyclohexanol is so low and concentration of cyclohexanol in water is so low (0.05 to 0.06%) that the oil phase containing unreacted cyclohexene scarcely contains cyclohexanol.

In comparison with alcohols derived from straight chain paraffins such as propylene or 1-butene, which exist in the aqueous phase due to their extremely strong affinity for water, the above-described oil solubility of cyclohexanol indicates a unique aspect of cyclic alcohols. In addition, this oil solubility influences the reactivity of cyclic olefin and the effect of fine-grained catalyst.

The thus-obtained cyclic alcohol in the oil phase containing unreacted cyclic olefin can be easily recovered by removing the cyclic olefin, which requires only a small latent heat of vaporization and which has a greatly different boilling point from that of cyclic alcohol. Thus, the recovery procedure is industrially quite advantageous. On the other hand, the fine-grained catalyst is confirmed not to be contained at all in the oil phase but completely exists in the aqueous phase. Various problems encountered in subjecting a slurry substance to separation procedures such as distillation are well known. The process of the present invention thus enables separation and recovery of the product absolutely without such procedure. Thus, the process of the present invention eliminates the difficulty in separation of the reaction product resulting from the use of fine-grained catalyst, and fully provides the effects of fine-grained catalyst.

Upon reaction, it is also effective to ionexchange the zeolites with a proton, ion of an alkaline earth metal (e.g., Mg, Ca, Sr, etc.), a rare earth metal (e.g., La, Ce, etc.), or a metal of group VIII (of the Periodic Table) (viz., Fe, Ni, Co, Ru, Rh, Pd, Os, Ir, Pt) for use as catalysts.

Cycloalkenes to be used in the present invention include cyclopentene, methylcyclopentene, cyclohexene, methylcyclohexene, cyclooctene, cyclododecene, etc.

As a reaction manner, generally used ones are employed such as fluidized bed process, batchwise stirring process, continuous process, etc. In view of equilibrium of the hydration reaction of olefin and depressing side reactions, the reaction temperature is advantageously low, but, in view of the reaction rate, higher reaction temperatures are advantageous. Thus, in the present invention, the reaction is usually conducted from 50° to 250° C., preferably from 70° to 200° C., and more preferably from 80° to 150° C. The reaction pressure is not particularly limited, but in view of the properties of the catalyst of the present invention, the reaction is carried out at a pressure under which the oil phase and the aqueous phase are formed.

The molar ratio of one reactant cyclic olefin to the other reactant water can be selected from a wide range, but they are added in amounts exceeding their solubility, that is, in amounts sufficient to form an oil phase and an aqueous phase. If cyclic olefin is used excessively, it takes too much time to raise the concentration of produced cyclic alcohol in the oil phase. Accordingly, in the present invention the weight ratio of olefin to water preferably falls within the range of from 0.001/1 to 100/1, particularly preferably from 0.01/1 to 10/1. Upon reaction, an inert gas such as nitrogen, hydrogen, carbonic acid gas or the like may be allowed to coexist in addition to the reactants of water and cyclic olefin.

In conducting the reaction batchwise, the weight ratio of cyclic olefin to the catalyst is preferably in the range of from 0.005/1 to 100/1, and more preferably from 0.05/1 to 10/1, and the reaction time is preferably from 5 to 600 minutes, and more preferably from 5 to 300 minutes. The catalyst is usually used as a slurry in water, and the concentration of the catalyst is preferably in the range of from 1 to 60%, and more preferably from 5 to 50%, based on the total weight of the aqueous phase. Upon reaction, aliphatic saturated hydrocarbons, aromatic hydrocarbons, alcohols, ketones, esters, halogen-containing organic compounds, sulfur-containing organic compounds, organic acids, etc., may be added in the reaction system. The amounts of these compounds very depending upon the kind of the coexisting compound, reaction temperature, etc., and they may be added in such amounts that the two phases of oil phase and aqueous phase are formed in the reaction system.

In conducting the reaction batchwise, the oil phase containing produced cyclic alcohol is separated from the reaction system by allowing the reaction system to stand after completion of the reaction to separate the reaction system into two phases, and removing the upper oil phase. The standing may be conducted at the reaction temperature or while cooling. The standing time required for forming the two phases is extremely short, and the phase separation is generally completed in several seconds to several minutes, depending upon the size of the reactor used. Of course, a longer time may be provided for the removal procedure. The procedure of removing the upper oil phase may e conducted in an open state after reducing the pressure to ordinary pressure and the temperature to ordinary temperature, but direct withdrawal of the oil phase while maintaining the reaction temperature and the pressure is also effective. After removal of the oil phase, cyclic olefin may be again added to the system to recycle to the reaction zone.

In the case of conducting the reaction in a continuous manner, part of the reaction solution is taken out of the reaction system, and introduced into a standing tank to conduct phase separation. The upper oil phase thus-formed is removed, whereas the lower aqueous phase is recycled to the reaction zone. In such procedures, all fine-grained zeolite particles are retained in the aqueous phase in an extremely well dispersed state, and can be used as a homogeneous liquid phase without problems of plugging or the like. It is also effective to provide a standing zone at the upper part within the reactor to conduct phase separation.

Recovery of the produced cyclic alcohol from the oil phase is usually effected by distillation. Distillation can be conducted in both a batchwise process and a continuous process. For example, in distillation conducted in a continuous manner, unreacted cyclic olefin is removed from the tower top, and cyclic alcohol is removed from the bottom of the distillation tower. When an oil phase obtained by reacting cyclohexene as cyclic olefin with water is distilled to separate cyclohexene from cyclohexanol using a distillation tower having a theoretical plate number of from 10 to 15 steps under ordinary pressure with a reflux ratio of 1, cyclohexanol free cyclohexane is obtained from the tower top, and cyclohexanol of 99.8% or more in purity is obtained from the bottom thereof. The thus-recovered unreacted cyclic olefin is preferably recycled to the reaction zone to reuse. In order to remove slight amounts of by-products, etc., contained in the cycloolefin, it is effective to purify part or all of the unreacted olefin before the reuse for the reaction.

According to the present invention, production of cyclic alcohols from cyclic olefins by direct hydration reaction can be conducted with remarkably higher conversion and selectivity than that of the prior art by using a catalyst zeolite having a ratio of external surface acid sites to total acid sites in number of 0.07/1 or more and recovering the produced alcohols from an oil phase of unreacted cyclic olefin. As a result, the present invention also solves the problem of separating extremely fine-grained catalyst.

The present invention will now be described in more detail by referring to the following examples and comparative examples.

MEASUREMENT OF ACID SITES

The population of external surface acid sites (acid sites outside micropores) and total acid sites were measured according to the following pulse adsorption method.

As measuring equipment, a gas chromatograph, GC-7A, and a data-processing apparatus, CR-1A (both made by Shimadzu Seisakusho Ltd.), were used. A sample (0.2 g to 1 g) was loaded in a SUS-made column of 4 mm in inside diameter and 80 mm in overall length, and the column was mounted to a sample-side flow path placed in a thermostatic chamber of the gas chromatograph. Helium gas was introduced into the column as a carrier gas at a flow rate of 50 ml/min and, at the same time, the temperature within the chamber was increased to 325° C. by heating. Two hours after heating, adsorption procedure was initiated. Portions of a definite amount (0.2 to 2 $\mu$l) of an amine (pyridine, 4-methylquinoline, or tributylamine) were intermittently injected at definite intervals (2 minutes to 5 minutes) through an injection opening on the sample-side flow path using a microsyringe. On the other hand, the carrier gas having traveled through the column was analyzed using a detector of FID (flame ionization detector) to obtain a chromatogram showing periodical peaks of amine. With the increase in number of injection, the amount of adsorbed amine nears a saturation level, and the amount of non-adsorbed amine increases. Thus, in the above-mentioned chromatogram, peak area $S_i$ corresponding to non-adsorbed amine in the i-th injection of amine (e.g., peak area $S_5$ corresponding to the non-adsorbed amine in the 5th injection of amine) gradually approaches the area $S_0$ which corresponds to the amount of injected amine, $d_0$ $\mu$mol. Therefore, the amount of adsorbed amine per unit weight of sample, $A_0$ (μmol/g), can be given by $$A_0 = \frac{1}{W} \sum_{i=1}^{\infty} \left(1 - \frac{S_i}{S_0}\right) d_0$$

wherein W (in grams) represents the weight of a sample.

In the present invention, injection was repeated n times at which $S_i/S_0 \geq 0.98$, and the amount of adsorbed amine, A (μmol/g), was calculated according to the following formula:

$$A = \frac{1}{W} \sum_{i=1}^{n} \left(1 - \frac{S_i}{S_0}\right) d_0$$

The population ratio of external surface acid sites to total acid sites of a particular zeolite was determined as follows. That is, with zeolite having a micropore diameter of a Å, an amount of adsorbed amine corresponding to external surface acid sites, $A_{out}$, is determined using amine I having a kinetic diameter of $a_1$ (>a), and an amount of adsorbed amine corresponding to total acid sites, $A_{total}$, is determined using amine II having a kinetic diameter of $a_2$ (<a). (Concerning "kinetic diameter", see D. W. Breck *Zeolite Molecular Sieves*, pp. 634–635, pub. Wiley-Interscience (1974).) The population ratio of external surface acid sites to total acid sites, R, can be calculated by the following formula:

$R = A_{out}/A_{total}$

For measuring the population ratio, R, a combination of pyridine and tributylamine was used in Examples 7, 8, 9, 10 and 11 and Comparative Examples 6, 7 and 8, and a combination of pyridine and 4-methyl-quinoline was used in the other Examples and Comparative Examples.

EXAMPLE 1

I. Preparation of Catalyst

Solution A and Solution B having the following formulations were prepared by stirring in a 5 liter beaker at room temperature.

| Solution A: | |
|---|---|
| Sodium Silicate (SiO₂ 28.8%, Na₂O 8.9%, H₂O 62.4%; Q-Brand sodium silicate) | 1,112 g |
| Water | 1,386 g |
| Solution B: | |
| Aluminum Sulfate | 32.2 g |
| Sodium Chloride | 328 g |
| Concentrated Sulfuric Acid | 92.6 g |
| Tetrapropylammonium Bromide | 139 g |
| Water | 1,896 g |

Solution A and Solution B were intimately mixed at room temperature in a high speed stirring homogenizer having an inside volume of 10 liters to prepare a reaction mixture (called "gel").

This mixture was charged in a 7 liter autoclave and, after displacing the atmosphere within the autoclave by nitrogen gas, the autoclave was closed and heated to a reaction temperature of 120° C. while stirring at a rate of 80 rpm. Then, the stirring speed was accelerated to 600 rpm, and the reaction temperature of 120° C. was kept for 72 hours, followed by heating to 160° C. The reaction temperature was kept at 160° C. for 5 hours while maintaining the stirring speed at the same level. Thereafter, heating was discontinued, and the autoclave was allowed to cool with stirring.

The reaction product cooled to room temperature was removed from the autoclave, washed with water until the residual chloride ion concentration became not more than 100 ppm (based on sample calcined at 500° C.), then dried at 130° C. The crystalline product was calcined in air for 5 hours at 550° C. in an as-produced powdery form. The thus-calcined powdery crystals were subjected to ion-exchanging by treating them three times each with 10 ml of a 2M aqueous solution of ammonium chloride per g of the crystals at a reaction temperature of 80° C. for 2 hours. Subsequently, the powdery crystals were washed with water at 80° C., then dried at 130° C., followed by calcination in the air at 400° C. for 2 hours.

The thus-obtained product was fine crystals and was identified as ZSM-5 by X-ray diffractiometry. A photographic picture taken by a scanning type electron microscope (×50,000) revealed that particle sizes of the primary particles of the fine crystals were distributed in the range of from 0.02 to 0.08 μm, with an average particle size being 0.04 μm. It was also shown that the primary particles agglomerated to form secondary particles of several μm in diameter.

The ratio of external surface acid sites to total acid sites was 0.45.

Composition analysis was conducted according to X-ray fluorometry using part of the product to obtain an SiO₂/Al₂O₃ molar ratio of 58/1. Further, surface composition analysis was conducted according to X-ray photoelectron spectroscopy (XPS) to obtain an SiO₂/Al₂O₃ molar ratio of 58/1 on the external surface of the crystals produced.

II. Hydration Reaction 20 g of the catalyst obtained above, 60 g of water, and 30 g of cyclohexene were charged in a 200 ml autoclave equipped with a stirrer, and the reaction was conducted at 120° C. for 15 minutes under stirring. Then, stirring was stopped and the reaction solution was cooled. When the autoclave was opened, the contents were found to separate into two layers. The upper oil layer was separated and analyzed according to gas chromatography to find that the oil phase contained 12.1 wt% cyclohexanol, but no other products. When this oil phase was distilled in a distillation tower having a theoretical plate number of 10 steps, packed with Dixon packing at a reflux ratio of 1 under normal atmospheric pressure, cyclohexene was distilled out of the tower through the top of the tower at 83° C. Distillation was continued until no distillates were produced. After completion of the distillation, 2.3 g of a residue was obtained from the bottom of the tower. Analysis of the residue by gas chromatography revealed that the purity of the product was 99.8%.

COMPARATIVE EXAMPLE 1

I. Preparation of Catalyst

A catalyst was prepared in the same manner as in Example 1 except for the following points.

| (1) Formulation of Solution A | |
|---|---|
| Q-Brand Sodium Silicate | 1,115 g |

-continued

| | |
|---|---|
| Water | 1,382 g |
| (2) Formulation of Solution B | |
| Aluminum Sulfate | 31.5 g |
| Sodium Chloride | 325 g |
| Tetrapropylammonium Bromide | 136 g |
| Concentrated Sulfuric Acid | 92.1 g |
| Water | 1,893 g |
| (3) Crystallizing Conditions | |

After charging the solutions to an autoclave, the mixture was heated to a reaction temperature of 165° C. while stirring at 80 rpm. Then, the stirring speed was accelerated to 200 rpm, and the reaction temperature of 165° C. was maintained for 48 hours.

The thus-obtained product was fine crystals and was identified as ZSM-5 by X-ray diffractiometry. A photographic picture taken by a scanning type electron microscope ($\times 10,000$) revealed that the average particle size of the crystals as primary particles was 6.5 $\mu$m. The ratio of external surface acid sites to total acid sites in number was 0.0055/1.

Composition analysis of the product according to X-ray fluorometry using part of the product indicated an $SiO_2/Al_2O_3$ molar ratio of 63/1. Further, surface composition analysis of the product according to X-ray photoelectron spectroscopy (XPS) using part of the product gave an $SiO_2/Al_2O_3$ molar ratio of 47/1 on the external surface of the produced crystals.

II. Hydration Reaction

The reaction was conducted under the same conditions as in Example 1, except for using the above-described catalyst. Thus, there was obtained an oil phase containing 1.3 wt% cyclohexanol and a trace amount of dicyclohexyl ether as a by-product.

COMPARATIVE EXAMPLE 2

Hydration reaction was conducted under the same conditions as in Example 1 except for using 20 g of 1-butene as reactant olefin and conducting the reaction for 4 hours. Conversion of 1-butene calculated from the 2-butanol produced was 0.73%, and most of the 2-butanol produced was in the water.

COMPARATIVE EXAMPLE 3

Hydration reaction was conducted under the same conditions as in Comparative Example 2 except for using the catalyst prepared in Comparative Example 1. Conversion of 1-butene was 0.61%, with most of the alcohol produced was in the water.

EXAMPLE 2

I. Preparation of Catalyst

A catalyst was prepared in the same manner as in Example 1 except for the following points.

| | |
|---|---|
| (1) Formulation of Solution A | |
| Q-Brand Sodium Silicate | 1,125 g |
| Water | 1,382 g |
| (2) Formulation of Solution B | |
| Aluminum Sulfate | 32.1 g |
| Sodium Chloride | 321 g |
| Tetrapropylammonium Bromide | 135 g |
| Concentrated Sulfuric Acid | 91.9 g |
| Water | 1,895 g |
| (3) Crystallizing Conditions | |

After charging Solution A and Solution B in the autoclave, the mixture was heated to a reaction temperature of 140° C. while stirring at 80 rpm. Then, the stirring speed was accelerated to 600 rpm, and the reaction temperature of 140° C. was kept for 36 hours.

The thus-obtained product was fine crystals and was identified as ZSM-5 by X-ray diffractiometry. A photographic picture taken by a scanning type electron microscope ($\times 20,000$) revealed that the average particle size of the crystals as primary particles was 0.45 $\mu$m. The ratio of external surface acid sites to total acid sites was 0.10/1.

Composition analysis of the product according to X-ray fluorometry using part of the product gave an $SiO_2/Al_2O_3$ molar ratio of 60/1. Further, surface composition analysis of the product according to X-ray photoelectron spectroscopy (XPS) using part of the product gave an $SiO_2/Al_2O_3$ molar ratio of 56/1 on the external surface of the produced crystals.

II. Hydration Reaction

The reaction was effected under the same conditions as in Example 1 except for using the above-prepared catalyst. Thus, there was obtained an oil phase containing 9.5 wt% cyclohexanol, with no other products being detected.

EXAMPLE 3

The reaction was conducted under the same conditions as in Example 1 except for changing the reaction time to 30 minutes, whereby an oil phase was obtained containing 16.1 wt% cyclohexanol, with no other products being detected.

EXAMPLE 4

The reaction was effected under the same conditions as in Example 1 except for changing the reaction temperature and the reaction time to 100° C. and 5 hours, respectively. Thus, an oil phase was obtained containing 22 wt% cyclohexanol and an aqueous phase containing 2 wt% cyclohexanol, with no other products being detected.

EXAMPLE 5

The reaction was effected under the same conditions as in Example 1 except for changing the reaction temperature and the reaction time to 170° C. and 1 hour, respectively. Thus, an oil phase was obtained containing 7.9 wt% cyclohexanol, 0.02 wt% dicyclohexyl ether, and 0.8 wt% methylcyclopentenes (mixture of isomers).

COMPARATIVE EXAMPLE 4

The reaction was effected under the same conditions as in Example 5 except for using the catalyst prepared in Comparative Example 1. Thus, there was obtained an oil phase containing 2.5 wt% cyclohexanol, 0.07 wt% dicyclohexyl ether, 3.8 wt% methylcyclopentenes, and 0.42 wt% high boiling product including cyclohexene dimer.

EXAMPLE 6

Only the oil phase was separated by decantation from the reaction mixture obtained in Example 4, and 30 g of reactant cyclohexene was newly added to the reactor retaining the catalyst-containing aqueous slurry phase. Then, the reaction was conducted under the same conditions as in Example 4. This procedure was repeated totally 50 times. The finally obtained oil phase contained 22 wt% cyclohexanol. Thus, almost no deterioration of catalytic activity and no reduction of sensitivity were observed.

COMPARATIVE EXAMPLE 5

The reaction was repeated 50 times under the same conditions as in Example 6 except for using the catalyst prepared in Comparative Example 1. The oil phase obtained by the first reaction run contained 2.4 wt% cyclohexanol, whereas the oil phase finally obtained by the final run contained only 1.2 wt% cyclohexanol.

EXAMPLE 7

I. Preparation of Catalyst

A catalyst was prepared generally in the same manner as in Example 1 except for the following points.

| (1) Formulation of Solution A | |
| --- | --- |
| Q-Brand Sodium Silicate | 1,036 g |
| Water | 1,009 g |
| (2) Formulation of Solution B | |
| Aluminum Sulfate | 108 g |
| Sodium Chloride | 303 g |
| Concentrated Sulfuric Acid | 52.1 g |
| Water | 1,710 g |
| Ethylpyridinium Bromide | 134 g |
| (3) Crystallizing Conditions | |

After charging the Solution A and Solution B in the autoclave, the mixture was heated to a reaction temperature of 155° C. while stirring it at 80 rpm. Then, the stirring speed was accelerated to 700 rpm, and the reaction temperature was kept at 155° C. for 54 hours. Further, the reaction temperature was raised to 185° C. and kept at that level for 4 hours while stirring at the same rate.

The thus-obtained product was fine crystals, which was identified as mordenite by X-ray diffractiometry. A photographic picture taken by a scanning type electron microscope (×50,000) revealed that the particle sizes of the crystals as primary particles were distributed between 0.02 and 0.07 μm, with the average particle size being 0.04 μm. The ratio of external surface acid sites to total acid sites in number was 0.43/1.

Composition analysis of the product according to X-ray fluorometry using part of the product gave an $SiO_2/Al_2O_3$ molar ratio of 21/1. Further, surface composition analysis according to X-ray photo-electron spectroscopy (XPS) using part of the product gave an $SiO_2/Al_2O_3$ molar ratio of 22/1 on the external surface of the crystals produced.

II. Hydration Reaction

The reaction was effected under the same conditions as in Example 1 except for using the above-prepared catalyst and changing the reaction temperature and the reaction time to 100° C. and 4 hours, respectively. Thus, there was obtained an oil phase containing 22.3 wt% cyclohexanol, with no other products being detected.

EXAMPLE 8

I. Preparation of Catalyst

A catalyst was prepared generally in the same manner as in Example 1 except for the following points.

| (1) Formulation of Solution A | |
| --- | --- |
| Q-Brand Sodium Silicate | 1,032 g |
| Water | 1,005 g |
| (2) Formulation of Solution B | |
| Aluminum Sulfate | 109 g |
| Sodium Chloride | 301 g |
| Concentrated Sulfuric Acid | 51.5 g |
| Water | 1,703 g |
| (3) Crystallizing Conditions | |

After charging Solution A and Solution B in the autoclave, the mixture was heated to a reaction temperature of 180° C. while stirring at 80 rpm. Then, the stirring speed was accelerated to 700 rpm, and the reaction temperature was kept at 180° C. for 20 hours.

The thus-obtained product was fine crystals and was identified as mordenite by X-ray diffractiometry. A photographic picture taken by a scanning type electron microscope (×10,000) revealed that the average particle size of the crystals was 0.41 μm or less as primary particles. The ratio of external surface acid sites to total acid sites in number was 0.11/1.

Composition analysis of the product according to X-ray fluorometry using part of the product gave an $SiO_2/Al_2O_3$ molar ratio of 23/1. Further, analysis of surface composition of the product according to X-ray photoelectron spectroscopy (XPS) using part of the product gave an $SiO_2/Al_2O_3$ molar ratio of 21/1 on the external surface of the crystals produced.

II. Hydration Reaction

The reaction was effected under the same conditions as in Example 1 except for using the above-prepared catalyst and changing the reaction time to 30 minutes. Thus, there was obtained an oil phase containing 10.0 wt% cyclohexanol, with no other products being detected.

COMPARATIVE EXAMPLE 6

I. Preparation of Catalyst

A catlyst was prepared in the same manner as in Example 1 except for the following points.

| (1) Formulation of Solution A | |
| --- | --- |
| Q-Brand Sodium Silicate | 1,030 g |
| Water | 1,001 g |
| (2) Formulation of Solution B | |
| Aluminum Sulfate | 110 g |
| Sodium Chloride | 303 g |
| Concentrated Sulfuric Acid | 51.0 g |
| Water | 1,705 g |
| (3) Crystallizing Conditions | |

After charging the Solution A and Solution B in the autoclave, the mixture was heated to a reaction temperature of 195° C. while stirring it at 80 rpm. Then, the stirring speed was accelerated to 200 rpm, and the reaction temperature was kept at 195° C. for 15 hours.

The thus-obtained product was fine crystals, which was identified as mordenite by X-ray diffractiometry. A photographic picture taken by a scanning type electron microscope (×2,000) revealed that the average particle size of the crystals was 20 μm as primary particles. The ratio of external surface acid sites to total acid sites in number was 0.0019/1.

Composition analysis of the product according to X-ray fluorometry using part of the product gave an $SiO_2/Al_2O_3$ molar ratio of 25/1. Further, analysis of the surface composition of the product according to X-ray photoelectron spectroscopy (XPS) using part of the product gave an $SiO_2/Al_2O_3$ molar ratio of 18/1 on the external surface of the crystals produced.

II. Hydration Reaction

The reaction was effected under the same conditions as in Example 7 except for using the above-prepared catalyst. Thus, there was obtained an oil phase containing 1.2 wt% of cyclohexanol.

EXAMPLE 9

I. Preparation of Catalyst 30 g of the catalyst prepared in Example 7 was added to a solution of 6.5 g of d,l-1,2-diphenylethylenediamine-N,N,N',N'-tetraacetic acid disodium salt in 1 l of water, and the mixture was stirred at a reaction temperature of 95° C. for 2 hours to react. After collecting the catalyst by filtration, it was dried at 130° C.

A photographic picture taken by a scanning type electron microscope (×10,000) revealed that particle sizes of the crystals as primary particles were distributed in the range of from 0.02 to 0.07 μm, with the average particle size being 0.04 μm. The ratio of external surface acid sites to total acid sites in number was 0.37/1.

Composition analysis of the product according to X-ray fluorometry using part of the product gave an $SiO_2/Al_2O_3$ molar ratio of 23/1. Further, analysis of surface composition of the product according to X-ray photoelectron spectroscopy (XPS) using part of the product gave an $SiO_2/Al_2O_3$ molar ratio of 34/1 on the external surface of the crystals produced.

II. Hydration Reaction

The reaction was effected under the same conditions as in Example 7 except for using the above-prepared catalyst and changing the reaction time to 3 hours. Thus, there was obtained an oil phase containing 22.8 wt% cyclohexanol, with no other products being detected.

EXAMPLE 10

I. Preparation of Catalyst

A catalyst was prepared generally in the same manner as in Example 1 except for the following points.

| (1) Formulation of Solution A | |
|---|---|
| Q-Brand Sodium Silicate | 947 g |
| Water | 957 g |
| (2) Formulation of Solution B | |
| Aluminum Sulfate | 231 g |
| Sodium Chloride | 310 g |
| Concentrated Sulfuric Acid | 46.5 g |
| Water | 1,725 g |
| (3) Crystallizing Conditions | |

After charging Solution A and Solution B of the above formulations in the autoclave, the mixture was heated to a reaction temperature of 180° C. while stirring it at 80 rpm. Then, the stirring speed was accelerated to 700 rpm, and the reaction temperature was kept at 180° C. for 20 hours.

The thus-obtained product was fine crystals, which was identified as mordenite by X-ray diffractometry. A photographic picture taken by a scanning type electron microscope (×10,000) revealed that the average particle size of the crystals was 0.2 μm or less as primary particles. The ratio of external surface acid sites to total acid sites was 0.21/1.

Composition analysis of the product according to X-ray fluorometry using part of the product gave an $SiO_2/Al_2O_3$ molar ratio of 10/1. Further, analysis of surface composition of the product according to X-ray photoelectron spectroscopy (XPS) using part of the product gave an $SiO_2/Al_2O_3$ molar ratio of 10/1 on the external surface of the crystals produced.

II. Hydration Reaction

The reaction was effected under the same conditions as in Example 7 except for using the above-prepared catalyst and changing the reaction time to 1 hour. Thus, there was obtained an oil phase containing 4.6 wt% of cyclohexanol, with no other products being detected.

COMPARATIVE EXAMPLE 7

I. Preparation of Catalyst

Proton type mordenite was prepared by ion-exchanging natural mordenite with a 2M ammonium chloride aqueous solution and calcining the ion-exchanged mordenite. A photographic picture taken by a scanning type electron microscope (×3,000) revealed that the average particle size of the crystals was 50 μm as primary particles. The population ratio of external surface acid sites to total acid sites was 0.0010/1.

Composition analysis of the product according to X-ray fluorometry using part of the product gave an $SiO_2/Al_2O_3$ molar ratio of 10/1. Further, analysis of surface composition of the product according to X-ray photoelectron spectroscopy (XPS) using part of the product gave an $SiO_2/Al_2O_3$ molar ratio of 13/1 on the external surface of the produced crystals.

II. Hydration Reaction

The reaction was effected under the same conditions as in Example 8 except for using the above-prepared catalyst and changing the reaction time to 1 hour. However, cyclohexanol was not produced at all.

EXAMPLE 11

I. Preparation of Catalyst

A catalyst was prepared in the same manner as in Example 1 except for the following points.

| (1) Formulation of Solution A | |
|---|---|
| Q-Brand Sodium Silicate | 918 g |
| Sodium Hydroxide | 150 g |
| Water | 3,018 g |
| Zeolite A (powder) | 21 g |
| A mixture of the above formulation was stirred at 100° C. for 4 hours to prepare Solution A. | |
| (2) Formulation of Solution B | |
| Sodium Aluminate | 96 g |
| Water | 540 g |
| (3) Crystallizing Conditions | |

After charging Solution A and Solution B of the above formulations in the autoclave, the mixture was heated to a reaction temperature of 100° C. while stirring it at 80 rpm. Then, the stirring speed was accelerated to 200 rpm, and the reaction temperature was kept at 100° C. for 5 hours.

The thus-obtained product was fine crystals, which was identified as faujasite by X-ray diffractometry. A photographic picture taken by a scanning type electron microscope (×50,000) revealed that the average particle size of the crystals was 0.1 μm or less as primary particles. The population ratio of external surface acid sites to total acid sites was 0.40/1.

Composition analysis of the product according to X-ray fluorometry using part of the product gave an $SiO_2/Al_2O_3$ molar ratio of 4.3/1. Further, analysis of surface composition of the product according to X-ray photoelectron spectroscopy (XPS) using part of the product gave an $SiO_2/Al_2O_3$ molar ratio of 3.9/1 on the external surface of the crystals produced.

II. Hydration Reaction

The reaction was effected under the same conditions as in Example 1 except for using the above-prepared catalyst and changing the reaction temperature and the reaction time to 170° C. and 1 hour, respectively. Thus, there was obtained an oil phase containing 3.5 wt% of cyclohexanol, with no other products being detected. Analysis of the aqueous phase conducted in the same manner revealed that it contained 0.81 wt% cyclohexanol.

COMPARATIVE EXAMPLE 8

I. Preparation of Catalyst

Proton type faujasite was prepared by ion-exchanging synthetic faujasite (type Y; made by Toyo Soda Manufacturing Co., Ltd.; $SiO_2/Al_2O_3=5.2/1$; average particle size: 2 μm) with a 2M ammonium chloride aqueous solution, and calcining the ion-exchanged faujasite.

The ratio of external acid sites to total acid sites was 0.02/1.

II. Hydration Reaction

The reaction was conducted under the same conditions as in Example 9 except for using the above-prepared catalyst. However, no cyclohexanol was detected.

Analysis of the aqueous phase revealed that it contained 0.02 wt% cyclohexanol.

EXAMPLE 12

I. Preparation of Catalyst

A catalyst was prepared in the same manner as in Example 1 except for the following points.

| (1) Formulation of Solution A | |
|---|---|
| Sodium Silicate (water glass No. 3 defined by JIS (Japanese Industrial Standard)) | 1,450 g |
| Water | 700 g |
| (2) Formulation of Solution B | |
| Aluminum Sulfate | 104 g |
| Concentrated Sulfuric Acid | 35 g |
| 1,3-Dimethylurea | 170 g |
| Water | 1,200 g |
| (3) Crystallizing Conditions | |

After charging Solution A and Solution B of the above formulations in the autoclave, the mixture was heated to a reaction temperature of 110° C. and kept at the temperature for 72 hours under stirring at a peripheral speed of 1.5 m/sec, then kept at a reaction temperature of 160° C. for 10 hours.

The thus-obtained product was fine crystals, and X-ray diffractiometry of the product showed a diffraction pattern analogous to that of ZSM-5.

A photographic picture taken by a scanning type electron microscope (×50,000) revealed that most of the crystals were hexagonal column crystals of 0.1 μm or less in shorter diameter (i.e., the minimum diameter dimension).

The $SiO_2/Al_2O_3$ molar ratio was determined to be 40/1 according to X-ray fluorometry, and the population ratio of external surface acid sites to total acid sites was determined to be 0.36/1 by the above adsorption method.

II. Hydration Reaction

The reaction was effected under the same conditions as in Example 1 except for using the above-prepared catalyst and changing the reaction time to 30 minutes. Thus, there was obtained an oil phase containing 11.5 wt% cyclohexanol, with no other products being detected.

EXAMPLE 13

I. Preparation of Catalyst

A catalyst was prepared in the same manner as in Example 1 except for the following points.

| (1) Formulation of Solution A | |
|---|---|
| Sodium Silicate (water glass No. 3) | 1,450 g |
| Water | 680 g |
| (2) Formulation of Solution B | |
| Aluminum Sulfate | 52 g |
| Concentrated Sulfuric Acid | 24 g |
| Acetonitrile | 80 g |
| Water | 1,200 g |
| (3) Crystallizing Conditions | |

After charging the autoclave with Solution A and Solution B of the above formulations, the mixture was kept at a reaction temperature of 120° C. for 72 hours, then, at a reaction temperature of 160° C. for 24 hours, while stirring it at a peripheral speed of 1.5 m/sec.

The thus-obtained product was fine crystals, and X-ray diffractiometry of the product showed a diffraction pattern analogous to that of ZSM-5.

A photographic picture taken by a scanning type electron microscope (×20,000) revealed that the crystals were hexagonal column crystals of 0.3 to 0.5 μm in shorter diameter.

The $SiO_2/Al_2O_3$ molar ratio was determined to be 50/1 according to X-ray fluorometry and analysis of high frequency induced bond emission (ICP), and the population ratio of external surface acid sites to total acid sites was determined to be 0.29/1 by the adsorption method.

II. Hydration Reaction

The reaction was effected under the same conditions as in Example 1 except for using the above-prepared catalyst and changing the reaction time to 30 minutes. Thus, there was obtained an oil phase containing 9.3 wt% cyclohexanol, with no other products being detected.

EXAMPLE 14

Hydration reaction of cyclohexene was conducted using a continuous flow type reactor as illustrated in the drawing.

That is, a 4 liter stainless steel reactor 3 equipped with a stirrer was charged with 600 g of the catalyst prepared according to the process described in Example 1 and 1,600 g of water, and the atmosphere within the reactor was displaced by a nitrogen gas, with the pressure being kept at 5 kg/cm². The temperature of the reactor was raised under stirring to a rate of 700 rpm, and, as the temperature reached 120° C., cyclohexene was introduced thereinto through feed pipe 1 at a rate of 800 g/hr including that recovered from discharge pipe 9, and makeup water was fed through feed pipe 2 by calculating the consumed amount of water based on the liquid level of the aqueous phase in separator 5. The reaction mixture taken out of the reactor 3 was then introduced into separator 5 via discharge pipe 4. The oil phase separated from the reaction mixture was introduced into distillator 8 via discharge pipe 6, whereas the aqueous phase was recycled to reactor 3 via recycle pipe 7. Gas chromatography of the oil phase discharged via discharge pipe 6 revealed that the concentration of cyclohexanol in the oil phase discharged 10 hours after initiation of feeding cyclohexene was 13.3 wt%, and that 1,000 hours after the initiation was 13.2 wt%. The distillator had 8 concentrating plates and 15 recovering plates, and was run at ordinary pressure and at a reflux ratio of 1. The bottom of the distillator was heated to 164° C. A low boiling fraction was distilled out of the distillator through the tower top thereof at 83° C., and recycled into reactor 3 via discharge pipe 9 and feed pipe 1. On the other hand, a high boiling fraction was withdrawn out of the bottom of the distillator 8 via discharge pipe 10. Gas chromatography of this high boiling fraction revealed the existence of 30 ppm of 1-methylcyclopentanol, 200 ppm of dicyclohexyl ether, 100 ppm of cyclohexanone, and trace amounts of 3-methylpantanol, etc. Purity of cyclohexanol in the high boiling fraction was 99.8%, with the balance of cyclohexene. Separately, this high boiling fraction was subjected to distillation under reduced pressure to examine non-volatile components, thus no inorganic matters including the catalyst being found. The low boiling fraction was partly introduced into purifier 12 via discharge pipe 11. Impurities mainly comprising methylcyclopentenes were removed via discharge pipe 14, whereas the purified low boiling fraction was recycled to discharge pipe 9 via purified liquid discharging pipe 13.

EXAMPLE 15

Hydration reaction was conducted under the same conditions as in Example 1 except for using 30 g of cyclopentene as the reactant olefin and conducting the reaction at 100° C. Analysis of the oil phase obtained after the reaction revealed that it contained 1.4 wt% cyclopentanol, with no other products being detected.

EXAMPLE 16

Hydration reaction was conducted under the same conditions as in Example 1 except for using 20 g of cyclooctene as the reactant olefin and conducting the reaction at 140° C. for 1 hour. Analysis of the oil phase obtained after the reaction revealed that it contained 2.6 wt% cyclooctanol, with no other products being detected.

EXAMPLE 17

A catalyst was prepared generally in the same manner as in Example 1 except for the following points.

| (1) Formulation of Solution A | |
|---|---|
| Silica Sol (30%) | 240 g |
| Water | 105 g |
| Sodium Hydroxide | 30 g |
| (2) Formulation of Solution B | |
| Boric Acid | 4.5 g |
| Tetrapropylammonium Bromide | 180 g |
| Water | 105 g |

Upon preparation of gel from Solutions A and B, pH was adjusted to 10.6 by adding concentrated sulfuric acid.

(3) Crystallizing Conditions

After charging the autoclave with the gel, the gel was heated to a reaction temperature of 100° C. while stirring at 80 rpm. Then, the stirring speed was accelerated to 1,200 rpm, while keeping the temperature at 100° C. for 135 hours. The contents were then heated to 160° C., and kept at the same temperature for 24 hours while maintaining the same stirring speed.

The thus-obtained product was fine crystals. The main diffraction pattern obtained by X-ray diffractiometry is given in Table 1. Scanning type electron microscopy revealed that particle sizes of the crystals were distributed in the range of from 0.1 to 0.5 μm, with the average particle size being 0.3 μm. The population ratio of external surface acid sites to total acid sites was 0.20/1.

TABLE 1

| 2θ (°) | Spacing d (Å) | Relative Intensity I/I$_0$ (%) |
|---|---|---|
| 7.93 | 11.14 | 81 |
| 8.85 | 9.99 | 51 |
| 13.95 | 6.34 | 14 |
| 14.84 | 5.97 | 19 |
| 15.99 | 5.54 | 14 |
| 20.41 | 4.35 | 9 |
| 20.94 | 4.24 | 14 |
| 23.26 | 3.82 | 100 |
| 23.97 | 3.71 | 49 |
| 24.52 | 3.63 | 33 |
| 26.01 | 3.42 | 9 |
| 27.02 | 3.30 | 10 |
| 29.41 | 3.04 | 11 |
| 30.10 | 2.97 | 14 |

II. Hydration Reaction

Hydration reaction was conducted in the same manner as in Example 1 except for using the above-prepared catalyst and changing the reaction time to 1 hour. Analysis of the oil phase obtained after the reaction showed that it contained 10.1 wt% cyclohexanol, with no other products being detected.

EXAMPLE 18

I. Preparation of Catalyst

A catalyst was prepared in the same manner as in Example 1 except for the following points.

A 20% aqueous solution of sodium hydroxide was dropwise added, with stirring, to a mixture of 128 g of silica sol ("Snowtex 30", made by Nissan Kagaku Co., Ltd.), 32 g of tetrapropylammonium bromide, 8.6 g of gallium nitrate nonahydrate salt and 110 g of water to adjust the pH to 12. After charging the mixture in the autoclave, the mixture was heated to a reaction temperature of 150° C. for 65 hours with stirring.

The thus-obtained product was fine crystals, and X-ray diffractiometry of the product showed a diffraction pattern analogous to that of ZSM-5.

A photographic picture taken by a scanning type electron microscope ($\times 20,000$) revealed that the average particle size of the crystals was from 0.2 to 0.3 μm.

The $SiO_2/Ga_2O_3$ molar ratio was determined to be 43/1 according to X-ray fluorometry, and the content of $Al_2O_3$ was too low to measure by the X-ray fluorometry. The population ratio of external surface acid sites to total acid sites was 0.24/1.

II. Hydration Reaction

The reaction was effected under the same conditions as in Example 1 except for using the above-prepared catalyst and changing the reaction time to 30 minutes. Thus, there was obtained an oil phase containing 11.9 wt% cyclohexanol, with no other products being detected.

While the invention has been described in detail and with reference to specific embodiments thereof, it will be apparent to one skilled in the art that various changes and modifications can be made therein without departing from the spirit and scope thereof.

What is claimed:

1. A process for producing a cyclohexanol by catalytic hydration of cyclohexene in a liquid phase, which comprises using as a catalyst a zeolite having a population ratio of acid sites on the external surface to total acid sites of 0.07/1 or more, conducting the hydration reaction in a reaction zone in the co-presence of an oil phase mainly containing the cyclohexene and an aqueous phase mainly containing water and the catalyst while controlling the cyclohexanol produced so that the concentration thereof in the oil phase is more than that in the aqueous phase, and separating and recovering the cyclohexanol produced from the oil phase, wherein the reaction is conducted at from 50° to 250° C.

2. A process as in claim 1, wherein said zeolite is a zeolite containing at least one of mordenite, faujasite, ZSM-type zeolite, borosilicate, ferrosilicate, chromosilicate, gallosilicate, AZ-1 and clinoptilolite.

3. A process as in claim 2, wherein said zeolite has a molar ratio of silica to alumina, boron, iron, chromium or gallium of 10/1 or more.

4. A process as in claim 3, wherein said zeolite has a molar ratio of silica to alumina, boron, iron, chromium or gallium of 20/1 or more.

5. A process as in claim 1, wherein the population ratio of acid sites on external surface to total acid sites is 0.2/1 or more.

6. A process as in claim 1, wherein the population ratio of acid sites on external surface to total acid sites is 0.3/1 or more.

7. A process as in claim 1, wherein said zeolite comprises primary particles of up to 0.5 μm in particle size.

8. A process as in claim 7, wherein said zeolite comprises primary particles of up to 0.1 μm in particle size.

9. A process as in claim 7, wherein said zeolite comprises primary particles of up to 0.05 μm in particle size.

10. A process as in claim 1, wherein said zeolite is partly or wholly ion exchanged with proton, an alkaline earth metal of Mg, Ca, or Sr, a rare earth metal of La or Ce, or a group VIII metal selected from Fe, Ni, Co, Ru, Rh, Pd, Os, Ir, and Pt.

11. A process as in claim 1, wherein the reaction is conducted at from 80° to 150° C.

12. A process as in claim 1, wherein said oil phase containing the cyclohexanol produced is fed to a distillation tower, cyclohexane is recovered from the tower top, and the cyclohexanol is recovered from the bottom of the tower.

13. A process as in claim 12, wherein said recovered cyclohexanol is recycled to the reaction zone.

14. A process as in claim 13, wherein said recovered cyclohexene is partly or wholly purified before being recycled to the reaction zone.

15. A process as in claim 1, wherein said cyclohexene is continuously fed to the reaction zone, and the produced cyclohexanol is continuously separated and recovered.

16. A process as in claim 15, wherein the oil phase containing the produced cyclohexanol and the aqueous phase are separated from each other outside of the reaction zone.

17. A process as in claim 1, wherein the zeolite contains at least one of mordenite, faujasite, ZSM-type zeolite, AZ-1, clinoptilolite, borosilicate, ferrosilicate, chromosilicate and gallosilicate, has a molar ratio of silica to alumina, boron, iron, chromium or gallium of 10/1 or more, and comprises primary particles of up to 0.5 μm in particle size; and the process is conducted at from 70° to 200° C.

* * * * *